US010119945B2

(12) United States Patent
Watando et al.

(10) Patent No.: US 10,119,945 B2
(45) Date of Patent: Nov. 6, 2018

(54) METHODS FOR RECOVERING AND ANALYZING AMINES

(71) Applicant: KABUSHIKI KAISHA TOSHIBA, Minato-ku (JP)

(72) Inventors: Hiroko Watando, Tokyo (JP); Takashi Kuboki, Tokyo (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 0 days.

(21) Appl. No.: 13/942,954

(22) Filed: Jul. 16, 2013

(65) Prior Publication Data

US 2014/0024127 A1    Jan. 23, 2014

(30) Foreign Application Priority Data

Jul. 18, 2012  (JP) ................ 2012-159628

(51) Int. Cl.
| | | |
|---|---|---|
| *G01N 30/96* | (2006.01) | |
| *C07C 213/10* | (2006.01) | |
| *B01D 15/00* | (2006.01) | |
| *C07C 241/00* | (2006.01) | |
| *B01D 53/14* | (2006.01) | |
| *B01J 39/17* | (2017.01) | |
| *B01J 49/06* | (2017.01) | |
| *B01J 49/53* | (2017.01) | |
| *B01J 49/60* | (2017.01) | |

(52) U.S. Cl.
CPC ............ *G01N 30/96* (2013.01); *B01D 15/00* (2013.01); *B01D 53/1418* (2013.01); *B01J 39/17* (2017.01); *B01J 49/06* (2017.01); *B01J 49/53* (2017.01); *B01J 49/60* (2017.01); *C07C 213/10* (2013.01); *C07C 241/00* (2013.01); *B01D 53/1475* (2013.01); *Y02C 10/06* (2013.01); *Y02C 10/08* (2013.01); *Y10T 436/147777* (2015.01); *Y10T 436/170769* (2015.01); *Y10T 436/173845* (2015.01)

(58) Field of Classification Search
CPC ................ B01D 15/00; B01D 53/1418; Y10T 436/173845; C07C 213/10; C07C 241/00; G01N 30/96; B01J 39/165; B01J 49/0008; B01J 49/0069
USPC ................... 436/98, 111, 107; 564/112, 497; 210/660
See application file for complete search history.

(56) References Cited

U.S. PATENT DOCUMENTS

| | | | |
|---|---|---|---|
| 2,797,188 A | 6/1957 | Taylor, Jr. et al. | |
| 3,433,841 A | 3/1969 | Dehn et al. | |
| 5,451,660 A * | 9/1995 | Builder ................... | C07K 1/20 530/300 |
| 8,506,913 B2 * | 8/2013 | Murai ................ | B01D 53/1475 252/184 |
| 2008/0207638 A1 | 8/2008 | Ancliff et al. | |
| 2009/0018029 A1 * | 1/2009 | Miao ................. | G01N 33/6812 506/9 |
| 2010/0108610 A1 * | 5/2010 | Godhwani et al. ......... | 210/670 |

FOREIGN PATENT DOCUMENTS

| | | |
|---|---|---|
| JP | S49-84977 A | 8/1974 |
| JP | 10-90240 | 4/1998 |
| JP | 11-90160 | 4/1999 |
| JP | 4101463 B2 | 6/2008 |
| JP | 2009-501744 | 1/2009 |
| JP | 2011-521781 | 7/2011 |
| JP | 2012-223681 | 11/2012 |
| WO | WO 2009/145372 A1 | 12/2009 |
| WO | WO 2011/027794 A1 | 3/2011 |
| WO | WO 2011/121633 A1 | 10/2011 |

OTHER PUBLICATIONS

Ancliff et al. Compounds. WO 2007/009739.*
Singh, N. et al. Benzimidazole: A short review of their antimicrobial activites.(2012). 5:119-127.*
Extended European Search Report dated Sep. 27, 2013 in Patent Application No. 13176179.3.
Pavel Jandera, et al, "Ion-Exchange Chromatography of Nitrogen Compounds" Journal of Chromatography, vol. 98, No. 1, XP055079494, Mar. 1, 1974, pp. 1-54.
Donald J. Pietrzyk, "Ion-Exchange Resins in Non-Aqueous Solvents—I," Talanta, vol. 13, No. 2, XP026580513, Feb. 1, 1966, pp. 209-223.
Vida Simat, et al., "Use of small diameter column particles to enhance HPLC determination of histamine and other biogenic amines in seafood" LWT—Food Science and Technology, vol. 44, No. 2, XP027445449, Mar. 1, 2011, pp. 399-406.
Office Action dated Jun. 13, 2014 in Japanese Patent Application No. 2012-159628 (with English translation).
Japanese Office Action dated Feb. 10, 2015 in corresponding Japanese Patent Application No. 2012-159628 filed Jul. 18, 2012 (with English translation).
Office Action dated Apr. 12, 2016 in Japanese Patent Application No. 2012-159628 (with unedited computer generated English language translation).

* cited by examiner

*Primary Examiner* — Rebecca M Fritchman
(74) *Attorney, Agent, or Firm* — Oblon, McClelland, Maier & Neustadt, L.L.P.

(57) ABSTRACT

The objects of embodiments in the present disclosure are to provide a method capable of recovering two or more amine compounds at the same time from a gas or solution, and also to provide a method capable of analyzing the recovered amines.
The amine-recovering method comprises the steps (A) and (B). In the step (A), the gas or solution is brought into contact with a solid adsorbent so that the adsorbent may retain the amines. In the step (B), the amines retained by the adsorbent in the step (A) are eluted out by use of a basic compound-containing organic solvent. The solid adsorbent has a substituent group represented by $—SO_3M$ (M is H or an alkali metal).

17 Claims, No Drawings

METHODS FOR RECOVERING AND ANALYZING AMINES

CROSS-REFERENCE TO RELATED APPLICATIONS

This application is based upon and claims the benefit of priority from the prior Japanese Patent Application No. 2012-159628, filed on Jul. 18, 2012, the entire contents of which are incorporated herein by reference.

FIELD

The present disclosure relates to methods for recovering and analyzing amines.

BACKGROUND

Recently, in order to prevent global warming, it has been required to reduce emission of carbon dioxide into atmosphere.

As one of the means for carbon dioxide capture and storage (hereinafter, often referred to as "CCS" in the present specification), there is a recovering method based on chemical adsorption. That recovering method has hitherto played an important role in reducing carbon dioxide contained in combustion gases exhausted from boilers in, for example, thermal power plants.

Specifically, a representative CCS process is carried out in the following manner.

First, a combustion gas exhausted from boilers is subjected to treatments, such as, denitration, dust collection, and desulfurization, according to necessity. The gas is then introduced into an absorption tower, in which the gas is brought into contact with an absorption solution so that $CO_2$ in the combustion gas may be absorbed therein and thereby removed from the combustion gas. The solution thus absorbing $CO_2$ is heated by means of, for example, a heat exchanger, and then introduced into a regeneration tower. In the regeneration tower, $CO_2$ is dissociated and recovered from the absorption solution. After experiencing dissociation of $CO_2$ in the regeneration tower, the absorption solution is circulated again into the absorption tower and reused for absorbing $CO_2$ in the combustion exhaust gas.

The absorption solution used in the above CCS process preferably comprises an amine and water.

In performing the above CCS process based on chemical adsorption, it is necessary to be so careful that the amine and degradation products thereof in the absorption solution may not leak out from the CCS apparatuses, such as, the absorption tower, the regeneration tower, and the like. For the purpose of that, it is required to provide methods for recovering and analyzing the amine serving as a component of the absorption solution and degradation products thereof. Specifically, as for nitrosoamines in particular, it is desired to provide techniques of high-level recovering and of highly-sensitive quantitative analysis because they are considered to be hazardous compounds.

DETAILED DESCRIPTION

An embodiment of the present disclosure resides in a method for recovering an amine contained in a gas or in a solution, comprising:

the step (A), in which said gas or solution is brought into contact with a solid adsorbent so that the adsorbent may retain the amine; and the step (B), in which the amine retained by the adsorbent in the step (A) is eluted out by use of a basic compound-containing organic solvent;

wherein said solid adsorbent has a substituent group represented by —$SO_3M$ in which M is H or an alkali metal.

The following will describe one of the most preferred examples of the present embodiment, and hence the present embodiment is by no means limited within the scope concretely described below.

<Method for Recovering an Amine>

The recovering method of the present embodiment is for the purpose of recovering an amine contained in a gas or in a solution, and comprises the step (A), in which the gas or solution is brought into contact with a solid adsorbent so that the adsorbent may retain the amine; and the step (B), in which the amine retained by the adsorbent in the step (A) is eluted out by use of a basic compound-containing organic solvent.

In the above method, the solid adsorbent has a substituent group represented by —$SO_3M$ (in which M is H or an alkali metal).

Here, "recovering an amine" does not mean simply isolating or removing an aimed amine from the gas or solution, but it means isolating or removing an aimed amine from the gas or solution and then collecting the amine in such a way that the amine does not undergo any essential chemical change between before and after the operations.

If desired, the "amine-recovering method" of the present embodiment enables to recover the amine in a higher concentration than when it was in the gas or solution. In that case, the "amine-recovering method" of the present embodiment can be also regarded as an "amine-concentrating method".

The amine-recovering method according to the present embodiment comprises the steps (A) and (B) described above. However, the method of the present embodiment is not limited to a process consisting of only the steps (A) and (B), and includes processes comprising other optional steps or treatments conducted according to necessity before the step (A), after the step (B) or between the steps (A) and (B). Further, each of the steps (A) and (B) does not need to be carried out throughout under the same conditions, and the conditions may be changed in the course of the step. If necessary, the procedure of each step can be stopped halfway and thereafter restarted.

<Step (A)>

In the step (A) of the amine-recovering method according to the present embodiment, a gas or solution containing the aimed amine is brought into contact with a solid adsorbent so that the adsorbent may retain the amine.

<<Gas or Solution Containing Amine (Part 1)>>

Examples of the amine to be recovered include: (i) primary amines, (ii) secondary amines, (iii) tertiary amines, (iv) cyclic amines, (v) other aliphatic amines, aromatic amines, multivalent amines, and alkanolamine compounds, (vi) amine derivatives, and (vii) mixtures thereof. The gas or solution to be treated may contain either only one amine or plural amines.

Preferred examples of the (i) primary amines include: monoethanolamine, 2-amino-1-propanol, 3-amino-1-propanol, 1-amino-2-propanol, 2-amino-1-butanol, 3-amino-1-butanol, 4-amino-1-butanol, 2-amino-2-methyl-1-propanol, 2-amino-2-ethyl-1-propanol, ethylenediamine, propylenediamine, ethylamine, 1-propylamine, 2-propylamine, and mixtures of two or more thereof.

Preferred examples of the (ii) secondary amines include: 2-methylaminoethanol, 2-ethylaminoethanol, diethanolamine, hydroxyethylhydroxypropylamine, dipropanolamine, isopropylaminoethanol, 3-methylamine-1,2-propanediol, diethylamine, methylethylamine, dipropylamine, and mixtures of two or more thereof.

Preferred examples of the (iii) tertiary amines include: dimethylaminoethanol, diethylaminoethanol, methyl diethanolamine, triethanolamine, 3-(dimethylamino)-1,2-propanediol, 2-{[2-(dimethylamino)ethyl]methylamino}ethanol, N,N,N',N'-tetramethylethylenediamine, and mixtures of two or more thereof.

Preferred examples of the (iv) cyclic amines include: piperidine, piperazine, 1-methylpiperazine, 2-methylpiperazine, 1,4-dimethylpiperazine, pyrrolidine, 1-methylpyrrolidine, 2-methylpyrrolidine, 1,4-diazabicyclo[2,2,2]octane, morpholine, and mixtures of two or more thereof.

Examples of the (vi) amine derivatives include: derivatives derived from amines of the above (i) to (v), such as, amine nitrites, amine nitrates, and other amine derivatives, in particular, nitrosoamines.

The concentration of amine in the gas is not particularly restricted, but is normally $1\times10^{-9}$ to $1$ g/m$^3$, preferably $1\times10^{-8}$ to $1\times10^{-1}$ g/m$^3$. The concentration of amine in the solution is not particularly restricted either, but is normally 1 ng/L to 100 mg/L, preferably 10 ng/L to 10 mg/L.

The present embodiment enables to increase the amine-recovering rate, which is a ratio of (total amount of recovered amines)/(total amount of amines contained in a gas or solution before the recovering procedures), to as high a rate as 90% or more, in particular, 94% or more.

<<Adsorbent>>

In the step (A) of the "amine-recovering method" according to the present embodiment, a gas or solution containing the aimed amine is brought into contact with a solid adsorbent so that the adsorbent may retain the amine. Here, "the adsorbent may retain the amine" means that the amine and the adsorbent may combine with each other via ionic bonds. Accordingly, if the amine is decomposed or denatured by contact with the solid adsorbent and hence cannot be readily recovered in such original form as was before the procedures, it cannot be said that the adsorbent retains the amine.

It is essential for the solid adsorbent to have a substituent group represented by —SO$_3$M (in which M is H or an alkali metal).

The alkali metal M may be any of lithium (Li), sodium (Na), potassium (K), rubidium (Rb), cesium (Cs) and francium (Fr). In view of the water-solubility and the treatability, M is preferably H or Na in the present embodiment.

In the present embodiment, the adsorbent in which M is H can be used in combination with that in which M is an alkali metal. Further, the adsorbents having different alkali metals can be employed in combination.

Among the above adsorbents, those having substituent groups represented by —R$^2$—SO$_3$M are preferred and further those having substituent groups represented by —R$^1$—R$^2$—SO$_3$M are particularly preferred. In the above formulas, M is H or an alkali metal; —R$^1$— is a substituent group represented by —[Si(CH$_3$)$_2$]— or —(CH$_2$)$_n$—; and —R$^2$— is a substituent group represented by —(CH$_2$)$_r$—, —(C$_6$H$_4$)$_s$— or —(CH$_2$)$_t$—(C$_6$H$_4$)$_u$—(CH$_2$)$_v$—; provided that n, r, s, t, u and v are integers satisfying the conditions of: $3 \le n \le 1000$, $5 \le r \le 24$, $1 \le s \le 3$, $0 \le t \le 24$, $0 \le u \le 3$, $0 \le v \le 24$ and $2 \le (t+u+v)$.

Preferred —R$^1$— is a substituent group represented by —[Si(CH$_3$)$_2$]— or —(CH$_2$)$_n$—; preferred —R$^2$— is a substituent group represented by —(C$_6$H$_4$)— or —(CH$_2$)—(C$_6$H$_4$)—; and n preferably satisfies the condition of $10 \le n \le 1000$.

The integers of n, r, s, t, u and v preferably satisfy the above conditions because amines can be recovered most efficiently when they are within the above ranges.

In the present invention, a particularly remarkable effect is given by the adsorbent having the following substituent group:

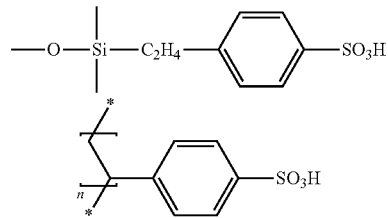

Because of the affinity with the amine-containing gas or solution, the above adsorbent can catch and retain the aimed amine selectively and efficiently.

There are no particular restrictions on the adsorbent support combined with the above substituent group as long as it can combine with the substituent group. Examples of the support include: silica gel, alumina, glass, kaolin, mica, talc, hydrated alumina, Wollastonite, iron powder, potassium titanate, titanium oxide, zinc oxide, silicon carbide, silicon nitride, calcium carbonate, carbon, barium sulfate, boron, ferrite, cellulose, and activated carbon.

The solid adsorbent may be in any form, such as, powder, granules, a sheet, or a cartridge, column or funnel filled with powder or granules. In view of the treatability, the solid adsorbent is preferably packed in a cartridge or column.

<<Contact of Gas or Solution with Solid Adsorbent>>

In the step (A) of the present embodiment, a gas or solution containing the amine is brought into contact with the solid adsorbent so that the adsorbent may retain the amine. In view of that, the solution preferably has a pH value of 1 to 7, more preferably 1 to 5, further preferably 2 to 5. For controlling the pH value of the sample containing the aimed compound, acids can be used.

Acids usable in the above are ones which do not react with the aimed amine in the above pH range and which are generally adopted as solvents. Examples thereof include: phosphoric acid, nitric acid, sulfuric acid, hydrochloric acid, acetic acid, formic acid, oxalic acid, lactic acid, citric acid, boric acid, butyric acid, methanesulfonic acid, ethanesulfonic acid, benzenesulfonic acid, chromic acid, hexafluorophosphoric acid, tetrafluorophosphoric acid, succinic acid, propionic acid, and mixtures thereof. If being too strong, the acid may have an effect on the adsorbent. Among the above, preferred are phosphoric acid, acetic acid and formic acid.

The temperature of this step for contact is not particularly restricted and hence is properly determined according to, for example, the kind of the amine, the kind and viscosity of the solution, and the kind of the solid adsorbent. However, it is generally 10 to 40° C.

There are also no particular restrictions on how the gas or solution containing the amine is brought into contact with the solid adsorbent, and it can be properly determined so that the object of the present embodiment can be achieved at a high level. However, in the present embodiment, the gas or solution containing the amine is preferably made to flow into a proper cartridge filled with the adsorbent in a powdery or granular form. It is possible to use two or more cartridges connected in series or in parallel. Those two or more cartridges are filled with the solid adsorbents which may be the same or different from each other in kind and/or in grain size.

If necessary, the gas or solution containing the amine may be pressured to promote the contact with the solid adsorbent.

<Step (B)>

In the step (B) of the present embodiment, the amine retained by the solid adsorbent in the step (A) is eluted out by use of a basic compound-containing organic solvent.

As the basic compound, any can be used as long as it essentially does not cause a chemical reaction with the aimed amine and is dissolvable in or miscible with the organic solvent. Preferred examples of the basic compound include: ammonia, sodium hydroxide, ammonium hydroxide, triethylamine, pyridine, histidine, diazabicycloundecene, and mixtures thereof. In the present embodiment, particularly preferred are ammonia and ammonium hydroxide. Since those are volatile compounds, they are advantageous in view of the analytical precision and damage to analytical apparatus in analyzing the recovered amine.

The concentration of the basic compound is preferably 0.5 to 10 wt % (provided that the total weight of the basic compound and the organic solvent is regarded as 100 wt %). If the concentration is less than 0.5 wt %, it is difficult to elute out efficiently the aimed compound retained by the solid adsorbent. On the other hand, even if the concentration is more than 10 wt %, the aimed amine can be eluted out. However, that is not preferred because the eluting solvent is so basic that the analytical apparatus may be damaged. It is hence particularly preferred for the basic compound to be contained in an amount of 1 to 5 wt %.

The organic solvent may be a normal organic solvent capable of dissolving the aimed compound and the basic compound. However, in view of the treatability and convenience in analyzing the eluted amine, the organic solvent preferably has low viscosity and a low boiling point. Examples thereof include: lower alcohols, such as, methanol, ethanol, and 2-propanol; acetone; and acetonitrile. Among them, methanol is most preferred in view of the solvency and the analytical precision and damage to analytical apparatus in analyzing the recovered amine. The basic compound-containing organic solvent may contain water or an aqueous solution containing an acid in an amount of 5 wt % or less. In that case, any can be used as the acid. Examples of the acid include: phosphoric acid, nitric acid, sulfuric acid, hydrochloric acid, acetic acid, formic acid, oxalic acid, lactic acid, citric acid, boric acid, butyric acid, methanesulfonic acid, ethanesulfonic acid, benzenesulfonic acid, chromic acid, hexafluorophosphoric acid, tetrafluorophosphoric acid, succinic acid, propionic acid, and mixtures thereof.

The step (B) can be carried out at a desired temperature. The temperature is properly determined according to, for example, the kind of the amine, the kind and viscosity of the solution, and the kind of the solid adsorbent. However, it is generally 10 to 40° C.

There are also no particular restrictions on how to elute out the amine retained by the solid adsorbent in the step (A), and it can be properly determined so that the object of the present embodiment can be achieved at a high level. For example, in the case where the adsorbent packed in a cartridge is used in the step (A), the basic compound-containing organic solvent is made to flow into the cartridge in the step (B). If necessary, after the step (A) and before the step (B), water or a solvent may be made to flow into the cartridge so as to wash the filler of the cartridge or to remove the solvent used in the step (A) from the cartridge.

If necessary, in the step (B), the basic compound-containing organic solvent may be pressured to promote the elution of the amine retained by the solid adsorbent.

In the present embodiment, as a result of the step (B), the amine is eluted out in the basic compound-containing organic solvent and thereby can be recovered.

The amine eluted out in the basic compound-containing organic solvent can be analyzed directly or after subjected to concentration treatment in which the basic compound and the organic solvent are at least partly removed away.

<Method for Analyzing the Amine>

The "amine-analyzing method" of the present embodiment is characterized by analyzing the amine recovered by the above amine-recovering method of the present embodiment.

The recovered amine can be analyzed in a desired manner capable of analyzing it. However, in view of the precision and the resolution, it is preferred to adopt high performance liquid chromatography, high performance liquid chromatograph-mass spectrometer, gas chromatograph flame ionization detector, or gas chromatograph-mass spectrometer. The conditions and operations for analyzing the amine can be properly determined according to the analytical apparatus, the analyzing procedures, the kind of the amine, and the like.

<Carbon Dioxide Capture and Storage (CCS)>

The "amine-recovering method" according to the present embodiment is advantageously employed for recovering an amine from an amine-containing gas or solution generated, for example, in CCS processes based on chemical adsorption, and also the "amine-analyzing method" of the present embodiment is useful for analyzing that gas or solution.

Specifically, it is particularly advantageous to employ the methods of the present embodiment for purposes of recovering and analyzing an amine contained in an "amine-containing gas or solution" used intentionally in the CCS processes (for example, an amine component used for preparing an amine-absorption solution) and/or an amine contained in another "amine-containing gas or solution" generated inevitably in the CCS processes (for example, an amine or a degradation product thereof vaporized or leaked out from the CCS apparatuses, such as, a solution-circulating system).

Accordingly, examples of the "amine-containing gas or solution" described above in <<gas or solution containing amine (part 1)>> include both of the "amine-containing gas or solution" used intentionally in the CCS processes and the "amine-containing gas or solution" generated inevitably in the CCS processes.

<<Gas or Solution Containing Amine (Part 2)>>

With respect to the gas or solution containing an amine used in the CCS processes, the description of <<gas or solution containing amine (part 1)>> will be further explained below in detail.

In the present embodiment, the "amine-containing gas or solution" contains an amine and water. It contains at least one amine, and may contain two or more amines. Preferably, it contains two to four kinds of amines. If two or more kinds of amines are used, they bring complementary effects that only one amine cannot realize and, as a result, they may improve performance of carbon dioxide capture and storage. On the other hand, if too many kinds of amines are used, it is often difficult to keep the performance in view of the apparatus operation. The amines are described above in <<gas or solution containing amine (part 1)>> in detail.

In the absorption solution containing water and one or more amines, the amount of primary amines is 50 to 100 wt %, preferably 70 to 96 wt %, based on the total weight of all the amines.

Accordingly, if primary amines are used in combination with other amines, the amount of other amines is 50 wt % or less. Any amine can be employed in combination with the primary amines.

The concentration of all the amines in the absorption solution is preferably 3.0 mol/L or more, further preferably 3.5 mol/L or more. If being less than 3.0 mol/L, the amine concentration is too low to expect high absorbability. On the other hand, as for the upper limit of the concentration, the solution may contain the amines in any high concentration as long as containing water. However, if the concentration is too high, the solution has such high viscosity as to lower the treatability and, in addition, the absorbability cannot be expected to be improved. It is hence proper for the concentration to be 6 mol/L or less.

If necessary, the absorption solution can contain a solvent other than water. Further, according to necessity, the solution also can contain other compounds, such as, antioxidants, pH controlling agents, antifoaming agents, preservatives, and corrosion inhibitor, in desired amounts.

<<Example of CCS>>

Preferred examples of the CCS processes based on chemical adsorption include: a carbon dioxide-recovering method comprising the step ($\alpha$), in which a gas containing carbon dioxide is brought into contact with an absorption solution containing an amine and water so that the absorption solution may absorb the carbon dioxide, and the step ($\beta$), in which the carbon dioxide absorbed in the absorption solution in the above step ($\alpha$) is dissociated from the solution.

In the step ($\alpha$), a carbon dioxide-containing gas, for example, a combustion gas from fossil fuel (such as, coal, petroleum, or LNG), is brought into contact with an absorption solution containing an amine and water so that the absorption solution may absorb the carbon dioxide. In this step, it is possible to adopt known carbon dioxide-absorbing systems, such as, a dispersed gas type-absorbing apparatus comprising a bubble agitation tank and a bubble tower, and a dispersed liquid type-absorbing apparatus comprising a spray tower, a spray chamber, a scrubber, a wetted wall tower, and a packed tower. In those systems, the carbon dioxide-containing gas can be brought into contact with the absorption solution containing an amine and water. In view of the carbon dioxide absorption efficiency, it is preferred to use a carbon dioxide-absorption tower filled with filler.

This step may be carried out at any reaction temperature as long as carbon dioxide can be absorbed. However, in view of the absorption rate and the absorption efficiency, the reaction temperature is preferably 25° C. to 70° C. inclusive, more preferably 30° C. to 60° C. inclusive.

In the step ($\beta$), the carbon dioxide absorbed in the absorption solution containing an amine and water in the above step ($\alpha$) is dissociated from the solution. As means for dissociating the carbon dioxide from the absorption solution containing an amine and water, the treatments of pressure reduction, heating and membrane separation are employable. However, they by no means restrict this step. However, the carbon dioxide can be easily dissociated by heating treatment. The heating treatment may be carried out at any temperature as long as the carbon dioxide can be dissociated, but the temperature is preferably 40° C. to 150° C. inclusive, more preferably 70° C. to 140° C. inclusive.

In the present embodiment, the absorption solution from which the carbon dioxide is thus dissociated can again absorb carbon dioxide and hence can be repeatedly used in the step for recovering carbon dioxide.

Preferred examples of the amines to which the "amine-recovering method" of the present embodiment can be applied include those used in the above carbon dioxide-recovering method comprising the steps ($\alpha$) and ($\beta$).

Further, preferred examples of the "amine-analyzing method" according to the present embodiment include a method for analyzing the amines recovered by the above carbon dioxide-recovering method comprising the steps ($\alpha$) and ($\beta$).

EXAMPLES

Among concrete examples of the present embodiment, preferred examples are selected and described below. Accordingly, the present embodiment is by no means limited within the scope concretely described below.

Example 1

Into a cartridge filled with a solid adsorbent having the functional group of

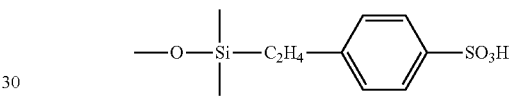

at the terminal, 5 mL of an aqueous solution containing 0.1 vol % of phosphoric acid and nitrosodimethylamine, nitrosodiethylamine, nitrosodiethanolamine, nitrosopiperazine, nitrosopiperidine, monoethanolamine, diethanolamine, and methyl diethanolamine each in an amount of 10 µg/mL was made to flow, so that the adsorbent retained the nitrosoamines and amines. Thereafter, the filler of the cartridge was washed with water and methanol to remove impurities, and then the nitrosoamines and amines retained by the adsorbent were eluted out and recovered by use of 5 mL of methanol containing 2 wt % of ammonia.

The eluted nitrosoamines and amines were analyzed by means of a gas chromatograph-mass spectrometer. As a result, it was confirmed that the amines were recovered in concentrations shown in Table 1.

Example 2

The procedure of Example 1 was repeated except for changing the concentration of phosphoric acid into 0.01 vol %, to recover and analyze the amines. The results were shown in Table 1.

Example 3

The procedure of Example 1 was repeated except for changing the concentration of phosphoric acid into 0.001 vol %, to recover and analyze the amines. The results were shown in Table 1.

Example 4

The procedure of Example 1 was repeated except for changing the concentration of phosphoric acid into 1 vol %, to recover and analyze the amines. The results were shown in Table 1.

Example 5

The procedure of Example 1 was repeated except for changing the concentration of ammonium into 1 wt %, to recover and analyze the amines. The results were shown in Table 1.

Example 6

The procedure of Example 1 was repeated except for changing the concentration of ammonium into 5 wt %, to recover and analyze the amines. The results were shown in Table 1.

Example 7

The procedure of Example 1 was repeated except for replacing the solid adsorbent with another solid adsorbent having the functional group of

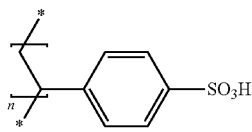

at the terminal, to recover and analyze the amines. The results were shown in Table 1.

Example 8

The procedure of Example 7 was repeated except for changing the concentration of phosphoric acid into 0.01 vol %, to recover and analyze the amines. The results were shown in Table 2.

Example 9

The procedure of Example 7 was repeated except for changing the concentration of phosphoric acid into 0.001 vol %, to recover and analyze the amines. The results were shown in Table 2.

Example 10

The procedure of Example 7 was repeated except for changing the concentration of phosphoric acid into 1 vol %, to recover and analyze the amines. The results were shown in Table 2.

Example 11

The procedure of Example 7 was repeated except for changing the concentration of ammonium into 1 wt %, to recover and analyze the amines. The results were shown in Table 2.

Example 12

The procedure of Example 7 was repeated except for changing the concentration of ammonium into 5 wt %, to recover and analyze the amines. The results were shown in Table 2.

Example 13

The procedure of Example 1 was repeated except for adopting a high performance liquid chromatograph-mass spectrometer in place of the gas chromatograph-mass spectrometer, to analyze the amines. The results were shown in Table 2.

Example 14

The procedure of Example 1 was repeated except for employing 5 mL of an aqueous solution containing 0.1 vol % of phosphoric acid and nitrosodimethylamine, nitrosodiethylamine, nitrosodiethanolamine, nitrosopiperazine, nitrosopiperidine, monoethanolamine, diethanolamine, methyl diethanolamine, 2-amino-2-methylethanol, methylaminoethanol, piperazine, piperidine, and morpholine each in an amount of 10 µg/mL, to recover and analyze the amines. The results were shown in Table 2.

Example 15

The procedure of Example 1 was repeated except for employing 5 mL of an aqueous solution containing the same amines as those in Example 1 but 1 vol % of acetic acid in place of the phosphoric acid, to recover and analyze the amines. The results were shown in Table 3.

Example 16

The procedure of Example 1 was repeated except for employing 50 mL of an aqueous solution containing 0.1 vol % of phosphoric acid and nitrosodimethylamine, nitrosodiethylamine, nitrosodiethanolamine, nitrosopiperazine, nitrosopiperidine, monoethanolamine, diethanolamine, and methyl diethanolamine each in an amount of 1 µg/mL, to recover and analyze the amines. The results were shown in Table 3.

Example 17

The procedure of Example 1 was repeated except for employing 500 mL of an aqueous solution containing 0.1 vol % of phosphoric acid and nitrosodimethylamine, nitrosodiethylamine, nitrosodiethanolamine, nitrosopiperazine, nitrosopiperidine, monoethanolamine, diethanolamine, and methyl diethanolamine each in an amount of 100 ng/mL, to recover and analyze the amines. The results were shown in Table 3.

Example 18

The procedure of Example 1 was repeated except for employing 5000 mL of an aqueous solution containing 0.1 vol % of phosphoric acid and nitrosodimethylamine, nitrosodiethylamine, nitrosodiethanolamine, nitrosopiperazine, nitrosopiperidine, monoethanolamine, diethanolamine, and methyl diethanolamine each in an amount of 10 ng/mL, to recover and analyze the amines. The results were shown in Table 3.

Example 19

The procedure of Example 1 was repeated except for employing 5 mL of an aqueous solution containing 0.1 vol % of phosphoric acid, 100 mg of pulverized coal, 0.1 mL of methanol, 100 ppm of iron ions, and nitrosodimethylamine, nitrosodiethylamine, nitrosodiethanolamine, nitrosopiperazine, nitrosopiperidine, monoethanolamine, diethanolamine, and methyl diethanolamine each in an amount of 10 μg/mL, to recover and analyze the amines. The results were shown in Table 3.

Example 20

The procedure of Example 1 was repeated except for employing 5 mL of an aqueous solution containing 5 vol % of phosphoric acid and nitrosodimethylamine, nitrosodiethylamine, nitrosodiethanolamine, nitrosopiperazine, nitrosopiperidine, monoethanolamine, diethanolamine, methyl diethanolamine, piperazine, and piperidine each in an amount of 10 μg/mL, to recover and analyze the amines. The results were shown in Table 3.

Example 21

The procedure of Example 1 was repeated except for changing the concentration of phosphoric acid into 0%, to recover and analyze the amines. The results were shown in Table 3.

Example 22

The procedure of Example 1 was repeated except for changing the concentration of ammonium into 0.1 wt %, to recover and analyze the amines. The results were shown in Table 4.

Example 23

The procedure of Example 1 was repeated except for changing the concentration of ammonium into 15 wt %, to recover and analyze the amines. The results were shown in Table 4.

Comparative Example 1

The procedure of Example 1 was repeated except for replacing the solid adsorbent with another solid adsorbent having a carboxylic acid group at the terminal, to recover and analyze the amines. The results were shown in Table 4.

Comparative Example 2

The procedure of Example 1 was repeated except for replacing the solid adsorbent with another solid adsorbent having a substituent group of —O—Si(CH$_3$)$_2$—C$_3$H$_6$—SO$_3$Na, to recover and analyze the amines. The results were shown in Table 4.

TABLE 1

|  | Ex. 1 | Ex. 2 | Ex. 3 | Ex. 4 | Ex. 5 | Ex. 6 | Ex. 7 |
|---|---|---|---|---|---|---|---|
| nitrosodimethylamine | 9.7 | 9.8 | 9.5 | 9.6 | 9.8 | 9.7 | 9.8 |
| nitrosodiethylamine | 9.5 | 9.6 | 9.4 | 9.6 | 9.4 | 9.8 | 9.4 |
| nitrosodiethanolamine | 9.8 | 9.8 | 9.6 | 9.8 | 9.6 | 9.6 | 9.6 |
| nitrosopiperazine | 10 | 9.9 | 9.9 | 9.8 | 9.7 | 9.9 | 9.8 |
| nitrosopiperidine | 9.8 | 9.5 | 9.6 | 9.6 | 10 | 9.7 | 9.9 |
| monoethanolamine | 9.7 | 9.6 | 9.4 | 9.7 | 9.5 | 9.5 | 9.5 |
| diethanolamine | 9.6 | 9.8 | 9.5 | 9.5 | 9.8 | 9.8 | 9.8 |
| methyl diethanolamine | 9.7 | 9.8 | 9.4 | 9.4 | 9.7 | 9.7 | 9.9 |
| 2-amino-2-methylethanol | — | — | — | — | — | — | — |
| methylaminoethanol | — | — | — | — | — | — | — |
| piperazine | — | — | — | — | — | — | — |
| piperidine | — | — | — | — | — | — | — |
| morpholine | — | — | — | — | — | — | — | recovered concentration [μg/mL]

TABLE 2

|  | Ex. 8 | Ex. 9 | Ex. 10 | Ex. 11 | Ex. 12 | Ex. 13 | Ex. 14 |
|---|---|---|---|---|---|---|---|
| nitrosodimethylamine | 9.7 | 9.7 | 9.8 | 9.6 | 9.7 | 9.6 | 9.8 |
| nitrosodiethylamine | 9.8 | 9.8 | 9.9 | 9.7 | 9.6 | 9.8 | 9.6 |
| nitrosodiethanolamine | 9.6 | 9.9 | 9.6 | 9.8 | 9.8 | 9.7 | 9.9 |
| nitrosopiperazine | 9.9 | 9.9 | 10 | 9.9 | 9.9 | 9.8 | 10 |
| nitrosopiperidine | 9.8 | 9.6 | 9.9 | 9.5 | 9.6 | 9.8 | 9.8 |
| monoethanolamine | 9.5 | 9.8 | 9.7 | 9.6 | 9.8 | 9.5 | 9.7 |
| diethanolamine | 9.6 | 9.8 | 9.6 | 9.8 | 9.9 | 9.7 | 9.6 |
| methyl diethanolamine | 9.7 | 9.9 | 9.8 | 9.9 | 9.7 | 9.6 | 9.8 |
| 2-amino-2-methylethanol | — | — | — | — | — | — | 9.6 |
| methylaminoethanol | — | — | — | — | — | — | 9.8 |
| piperazine | — | — | — | — | — | — | 9.9 |
| piperidine | — | — | — | — | — | — | 9.6 |
| morpholine | — | — | — | — | — | — | 9.8 | recovered concentration [μg/mL]

TABLE 3

|  | Ex. 15 | Ex. 16 | Ex. 17 | Ex. 18 | Ex. 19 | Ex. 20 | Ex. 21 |
|---|---|---|---|---|---|---|---|
| nitrosodimethylamine | 9.8 | 9.9 | 9.8 | 9.7 | 9.8 | 6.5 | 0.2 |
| nitrosodiethylamine | 9.6 | 9.7 | 9.7 | 9.6 | 9.9 | 7 | 0.1 |
| nitrosodiethanolamine | 9.7 | 9.8 | 9.6 | 9.4 | 9.7 | 5.9 | 0.2 |
| nitrosopiperazine | 9.9 | 10 | 9.8 | 9.8 | 9.9 | 6.8 | 0.6 |
| nitrosopiperidine | 9.8 | 9.8 | 9.8 | 9.4 | 9.8 | 7.5 | 0.9 |
| monoethanolamine | 9.6 | 9.9 | 9.7 | 9.6 | 9.7 | 6.3 | 0.7 |
| diethanolamine | 9.8 | 9.7 | 9.8 | 9.8 | 9.8 | 4.8 | 0.6 |
| methyl diethanolamine | 9.7 | 9.8 | 9.7 | 9.7 | 9.6 | 5.5 | 0.2 |
| 2-amino-2-methylethanol | — | — | — | — | — | — | — |
| methylaminoethanol | — | — | — | — | — | — | — |
| piperazine | — | — | — | — | — | 9.5 | — |
| piperidine | — | — | — | — | — | 8.7 | — |
| morpholine | — | — | — | — | — | — | — | recovered concentration [μg/mL]

TABLE 4

|  | Ex. 22 | Ex. 23 | Com. 1 | Com. 2 |
|---|---|---|---|---|
| nitrosodimethylamine | 8.7 | 9.5 | 1.8 | 0.9 |
| nitrosodiethylamine | 8.2 | 9.6 | 2.3 | 3.1 |
| nitrosodiethanolamine | 7.8 | 9.7 | 0.9 | 2.6 |
| nitrosopiperazine | 9.3 | 9.9 | 3.6 | 2.5 |
| nitrosopiperidine | 7.4 | 9.4 | 2.4 | 3 |
| monoethanolamine | 5.8 | 9.4 | 1.8 | 1.7 |
| diethanolamine | 6.9 | 9.3 | 5.8 | 6.4 |
| methyl diethanolamine | 8.2 | 9.8 | 6.3 | 5.8 |
| 2-amino-2-methylethanol | — | — | — | — |
| methylaminoethanol | — | — | — | — |
| piperazine | — | — | — | — |
| piperidine | — | — | — | — |
| morpholine | — | — | — | — | recovered concentration [μg/mL]

The amine-recovering method of the present embodiment enables to surely recover an amine from an amine-containing gas or solution essentially without decomposing or losing it. Further, even if two or more kinds of amines are contained in the gas or solution, they can be recovered at the same time by only one operation. Accordingly, the amines can be readily and very efficiently recovered by use of the method of the present embodiment.

The amine-recovering method according to the present embodiment is suitably employed for recovering amines and derivatives thereof, particularly, for recovering nitrosoamines, and hence can be used in many fields where various amines are recovered.

One of the fields in which the present embodiment can be used is, for example, carbon dioxide capture and storage technology. In the field of that technology, various amines required to be recovered can be simultaneously recovered with the same recovery apparatus and/or by the same recovery operation according to the present embodiment.

Further, the present embodiment enables to recover the amines in higher concentrations than when they were in the medium to be treated (namely, in the amine-containing gas or solution), and hence is very advantageous when the recovered amines are reused or discarded.

In addition, the amine-analyzing method of the present embodiment makes it possible that various amines recovered by the above amine-recovering method can be simultaneously analyzed with the same analytical apparatus and/or by the same analytical operation. Accordingly, the amines can be readily and very efficiently analyzed by use of the method of the present embodiment.

The amines to be analyzed are concentrated more than when they were in the medium to be treated (namely, in the amine-containing gas or solution), and hence from the results of the analysis it is easy to estimate sensitively and precisely the amine concentrations in the medium to be treated. For example, it is possible to analyze each amine concentration quantitatively at the ppb level.

The amine-recovering and analyzing methods according to the present embodiment greatly contribute to, for example, safe and stable operation of CCS plants.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fail within the scope and spirit of the inventions.

The invention claimed is:

1. A method for recovering at least one nitrosamine contained in a solution, comprising:
controlling a pH value of solution in the range of from 1 to 7 and bringing the solution into contact with a solid adsorbent packed in a cartridge or column so that the solid adsorbent retains the at least one nitrosamine, the solid adsorbent comprising an adsorbent support and a substituent group combining with the adsorbent support, said adsorbent support being selected from the group consisting of silica gel, alumina, glass, kaolin, mica, talc, hydrated alumina, Wollastonite, iron powder, potassium titanate, titanium oxide, zinc oxide, silicon carbide, silicon nitride, calcium carbonate, carbon, barium sulfate, boron, ferrite, cellulose, and activated carbon, and
said substituent group being represented by —$(CH_2)_w$—$C_6H_4$—$SO_3H$ or —$Si(CH_3)_2$—$CH_2$—$C_6H_4$—$SO_3H$, wherein w is an integer satisfying the condition of 4≤w≤1000; and
eluting out the at least one nitrosamine retained by the solid adsorbent with a basic compound-containing organic solvent, wherein said eluting is performed while applying a pressure,
wherein the organic solvent is selected from the group consisting of methanol, ethanol, 2-propanol, and acetone.

2. The method according to claim 1,
wherein the basic compound-containing organic solvent is methanol comprising ammonia in an amount of 0.5 to 10 wt %.

3. The method according to claim 1,
wherein the basic compound-containing organic solvent further comprises:
water or
an aqueous solution comprising an acid in an amount of 5 wt % or less.

4. The method according claim 1,
wherein the solid adsorbent is in the form of a column.

5. The method according to claim 1,
wherein the at least one nitrosamine was previously used in a carbon dioxide-recovering method comprising:
bringing a gas containing carbon dioxide into contact with a basic absorption solution so that the basic absorption solution absorbs the carbon dioxide, and
dissociating the carbon dioxide absorbed in the basic absorption solution from the basic absorption solution.

6. The method according to claim 1, the method further comprising:
analyzing at least one nitrosamine recovered;
wherein the at least one nitrosamine is analyzed in a manner selected from the group consisting of high performance liquid chromatography, high performance liquid chromatography-mass spectrometry, gas chromatograph flame ionization detection, and gas chromatograph-mass spectrometry.

7. The method according to claim 1,
wherein the at least one nitrosamine is in the solution.

8. The method of claim 1,
wherein the substituent group of the solid adsorbent is —$(CH_2)_w$—$C_6$—$SO_3H$ wherein w is an integer satisfying the condition of 4≤w≤1000.

9. The method of claim 1,
wherein the substituent group of said solid adsorbent is $Si(CH_3)_2$—$CH_2$—$C_6H_4$—$SO_3H$.

10. The method according to claim 1,
wherein the solution further comprises at least one additional amine.

11. The method according to claim 1,
wherein the pH of solution is from 1 to 5.

12. The method according to claim 3,
wherein said basic compound-containing organic solvent further comprises:
an aqueous solution comprising phosphoric acid in an amount of 5 wt % or less.

13. The method according to claim 1,
wherein a basic compound of the basic compound-containing organic solvent is not a pyridine.

14. The method according to claim 1, wherein the organic solvent comprises methanol.

15. The method according to claim 1, wherein the organic solvent comprises ethanol.

16. The method according to claim 1, wherein the organic solvent comprises 2-propanol.

17. The method according to claim 1, wherein the organic solvent comprises acetone.

* * * * *